(12) United States Patent
Gumbrecht et al.

(10) Patent No.: US 10,822,654 B2
(45) Date of Patent: Nov. 3, 2020

(54) SEQUENCING BIOPOLYMERS

(71) Applicant: SIEMENS AKTIENGESELLSCHAFT, Munich (DE)

(72) Inventors: Walter Gumbrecht, Herzogenaurach (DE); Oliver Hayden, Herzogenaurach (DE); Meinrad Schienle, Ottobrunn (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 473 days.

(21) Appl. No.: 14/910,990

(22) PCT Filed: May 8, 2014

(86) PCT No.: PCT/EP2014/059468
§ 371 (c)(1),
(2) Date: Feb. 8, 2016

(87) PCT Pub. No.: WO2015/018541
PCT Pub. Date: Feb. 12, 2015

(65) Prior Publication Data
US 2016/0186254 A1 Jun. 30, 2016

(30) Foreign Application Priority Data
Aug. 8, 2013 (DE) .................. 10 2013 215 666

(51) Int. Cl.
*G01N 33/48* (2006.01)
*G01N 33/50* (2006.01)
(Continued)

(52) U.S. Cl.
CPC ......... *C12Q 1/6874* (2013.01); *C12Q 1/6869* (2013.01); *G01N 33/48721* (2013.01);
(Continued)

(58) Field of Classification Search
None
See application file for complete search history.

(56) References Cited

U.S. PATENT DOCUMENTS 4,061,560 A * 12/1977 Hannig ............ G01N 27/44769
204/600
4,622,467 A * 11/1986 Britten ..................... H01J 47/14
250/374
(Continued)

FOREIGN PATENT DOCUMENTS

CN       102405410 A       4/2012
DE   102008008500 B3       9/2009
(Continued)

OTHER PUBLICATIONS

Ayub, Mariam et al., "Precise electrochemical fabrication of sub-20 nm solid-state nanopores for single-molecule biosensing," Journal ov Physics: Condensed Matter, vol. 22, No. 45, pp. 1-8, 2010.
(Continued)

*Primary Examiner* — Russell S Negin
(74) *Attorney, Agent, or Firm* — Lempia Summerfield Katz LLC (57) ABSTRACT

The invention relates to a method and a corresponding arrangement for sequencing at least two biopolymers (6), wherein for each biopolymer (6) a sequence signal is picked up by a respective measured variable pickup on the basis of the sequence of the biopolymer (6), the sequence signals are transferred to a shift register (16) and buffer-stored therein, the buffer-stored sequence signals are transferred from the shift register (16) sequentially to an evaluation device (26) and evaluated therein. Each sequence signal is preferably produced here by means of a nanopore arrangement (10). A corresponding sequencing arrangement (11) has the measured variable pickups and the shift register (16) integrated in it, preferably in an electrical circuit, that is to say on a
(Continued)

sensor array, for example. Each sequence signal can be amplified here by a preamplifier (14) prior to transfer to the shift register (16). The transfer of the output signal (A) to the evaluation device (24) can comprise the amplification of the signal by an output amplifier (24) and/or at least one EMCCD stage (32).

16 Claims, 5 Drawing Sheets

(51) Int. Cl.

| | | |
|---|---|---|
| *C12Q 1/6874* | (2018.01) | |
| *G01N 33/487* | (2006.01) | |
| *G11C 27/04* | (2006.01) | |
| *G11C 13/00* | (2006.01) | |
| *G11C 19/00* | (2006.01) | |
| *C12Q 1/6869* | (2018.01) | |

(52) U.S. Cl.
CPC .......... *G11C 13/0019* (2013.01); *G11C 19/00* (2013.01); *G11C 27/04* (2013.01)

(56) References Cited

U.S. PATENT DOCUMENTS

| | | | |
|---|---|---|---|
| 2003/0135332 A1 | 7/2003 | Shackleford | |
| 2007/0281288 A1* | 12/2007 | Belkin | B01L 3/502715 |
| | | | 435/4 |
| 2008/0109461 A1* | 5/2008 | Birdwell | G06F 16/2264 |
| 2010/0301398 A1* | 12/2010 | Rothberg | G01N 27/4145 |
| | | | 257/253 |
| 2010/0330553 A1* | 12/2010 | Su | C12Q 1/6874 |
| | | | 435/6.15 |
| 2011/0059864 A1* | 3/2011 | Farinas | C12Q 1/6872 |
| | | | 506/12 |

FOREIGN PATENT DOCUMENTS

| | | |
|---|---|---|
| EP | 0992869 A2 | 4/2000 |
| WO | WO2008086440 A2 | 7/2008 |
| WO | WO2008104136 A1 | 9/2008 |
| WO | WO2010112264 A1 | 10/2010 |
| WO | WO2010122293 A1 | 10/2010 |
| WO | WO2013130635 A2 | 9/2013 |

OTHER PUBLICATIONS

Branton, D. et al.: "The potential and challenges of nanopore sequencing," Nat Biotechnol, vol. 26 (No. 10), pp. 1146-1153, 2008.

Carminati, M. et al.: "Low-Noise Dual-Channel Currtent Amplifier for DNA Sensing with Solid-State Nanopores," 19th IEEE International Conference Electronics, Circuits and Systems (ICECS), pp. 817-820, 2012.

German Search Report for German Application No. 102013215666. 9, dated Sep. 3, 2013, with English Translation.

Liu, Q. et al: "Voltage-driven translocation of DNA through a high throughput conical solid-state nanopore," PLoS One vol. 7 (No. 9) e46014. 1-9, 2012.

Rosenstein, J.K. et al.: "Integrated nanopore sensing platform with submicrosecond temporal resolution," Nature methods, vol. 9, pp. 487-492, 2012.

Tsutsui, Makusu et al.: "Identiyfying single nucleotides by tunelling current nature nanotechnology," vol. 5, pp. 286-290, Apr. 2010.

Yukimoto, N. et al.: "Tracking single-particle dynamics via combined optical and electrical sensing," Sci. Rep. 3: 1855, pp. 1-7, 2013.

European Search Report for European Application No. 16190483.4, dated Feb. 24, 2017, with English Translation.

* cited by examiner

SEQUENCING BIOPOLYMERS

This application is the National Stage of International Application No. PCT/EP2014/059468, filed May 8, 2014, which claims the benefit of German Patent Application No. DE 10 2013 215 666.9, filed Aug. 8, 2013. The entire contents of these documents are hereby incorporated herein by reference.

BACKGROUND

The present embodiments relate to sequencing at least two biopolymers.

When sequencing a biopolymer (e.g., a nucleic acid or a protein), the sequence of the individual building blocks of the biopolymer (e.g., the nucleotide sequence (or base sequence) or the amino acid sequence) may be analyzed.

During sequencing (e.g., with the aid of nanopores), the biopolymer passes through a biological or artificial nanopore. Individual building blocks of the biopolymer may be analyzed by the nanopore as a result of a change in the pore resistance as the building blocks pass through. When different building blocks pass through the nanopore, a current conducted through the nanopore changes, for example. This change is dependent on the building block that passes through the pore, such that, for example, an individual nucleotide may be detected and, for example, the sequence of the nucleic acid may be determined.

Alternatively, a tunneling current may be measured in the nanopore, the tunneling current occurring only when the biopolymer passes through. The current intensity of the tunneling current is dependent on, for example, the nucleotide or the amino acid that is situated in the nanopore.

The difficulty, for example, when measuring the tunneling current results from the low intensity thereof in the nano-amperes range and also the relatively high capacitance of the tunnel electrodes. The capacitance arises as a result of parasitic capacitances with respect to the silicon of a silicon wafer on which the nanopore structure may be arranged, and with respect to the surrounding liquid that is in direct contact with the electrodes. Consequently, measuring the tunneling current necessitates preamplifiers that have a current input withstand a relatively high input capacitance (M. Carminati, G. Ferrari, M. Sampietro, A. P. Ivanov, T. Albrecht: "Low-Noise Dual-Channel Current Amplifier for DNA Sensing with Solid-State Nanopores," 19th IEEE International Conference Electronics, Circuits and Systems (ICECS) 2012, 817-820).

The article by Carminati et al. describes suitable discrete circuits for measurement on individual micropores. The publication by Rosenstein et al. (J. K. Rosenstein, M. Wanunu, C. A. Merchant, M. Drndic, K. Shepard: "Integrated nanopore sensing platform with sub-microsecond temporal resolution," Nature methods, 9, 2012, 487-492) describes the use of a complementary metal-oxide semiconductor (CMOS) sensor for detecting a tunneling current.

With the methods described in the prior art, the throughput of sequencings of a plurality of samples is not as high as desired, however. Sequence signals (e.g., signals detected by a measurement variable pick-up depending on a detected building block of a biopolymer) have a low current intensity and a small quantity of charge and are often superposed by noise. This problem also arises in other sequencing methods (e.g., in ion semiconductor DNA sequencing systems).

SUMMARY AND DESCRIPTION

The scope of the present invention is defined solely by the appended claims and is not affected to any degree by the statements within this summary.

The present embodiments may obviate one or more of the drawbacks or limitations in the related art. For example, the efficiency of sequencings of biopolymers is increased.

The present embodiments are based on the concept of combining an arrangement for sequencing (e.g., a nanopore arrangement) with principles from image sensor technology. As a result, a number of biopolymers may be simultaneously sequenced in parallel with a low circuit outlay.

The method according to one or more of the present embodiments correspondingly serves for sequencing at least two biopolymers (e.g., a plurality of identical or different nucleic acids or proteins) including the following acts. For each biopolymer, a sequence signal is picked up by a respective measurement variable pick-up depending on the sequence of the biopolymer. Each sequence signal is transferred in parallel into a shift register, and each sequence signal is buffer-stored by the shift register. The buffer-stored sequence signals are sequentially transferred from the shift register into an evaluation device (e.g., a microprocessor of a computer. The sequence signals are evaluated by the evaluation device.

In this case, a shift register may be an analog bucket brigade device (e.g., a switching mechanism) in which a plurality of multivibrators connected in series shift along stored content by one multivibrator upon each operating clock cycle according to the bucket brigade principle. One example of a shift register is a CCD image sensor.

Sequentially transferring each outgoing sequence signal of a measurement variable pick-up includes transferring into a respective multivibrator of a shift register. As a result, the shift register, via multivibrators of the shift register, may receive sequence signals from measurement variable pick-ups connected upstream in parallel. This makes it possible to multiply the number of simultaneously usable arrangements for sequencing (e.g., to multiply the number of simultaneous sequencings).

In this case, a sequence signal may describe a current intensity or a voltage value. The use of a shift register ensures noise-free and low-loss charge transfer. In addition, a plurality of biopolymers may be sequenced simultaneously, and the sequence signals of the different biopolymers may be "collected" (e.g., detected at the different measurement pick-ups, in parallel or simultaneously).

In one embodiment of the method, transferring each sequence signal into a shift register, which together with the measurement variable pick-up forms an integrated electrical circuit, is carried out, for example, on a sensor array as microchip. This enables simultaneous sequencing of the biopolymers and simultaneous reading-out of the signals for a number of identical or different biopolymers. In this case, picking up the sequence signal of the first biopolymer may be carried out at the same time as picking up the sequence signal of the further biopolymer. The simultaneous reading-out of the signals is made possible as a result.

Very fast sequencing is made possible as a result. A sequencing may be carried out by the integrated arrangement in less than one hour, for example.

Picking up the sequence signal with the aid of a nanopore arrangement including a respective nanopore for sequencing one of the biopolymers constitutes one embodiment of the method. A sequencing method with the aid of a nanopore arrangement enables a better resolution compared with other methods. The respective sequence signal may then describe, for example, a tunneling current that flows in the nanopore when the biopolymer passes through the nanopore. Tunneling current methods have a better resolution in comparison with, for example, measuring a pore resistance on account of high electric field strengths within the nanopore.

In accordance with a further embodiment, additional amplification of each sequence signal may be achieved by a respective preamplifier before the sequence signal is transferred into the shift register.

In a further embodiment of the method, sequentially transferring the buffer-stored sequence signals includes singly or multiply amplifying each sequence signal by one or a plurality of output amplifiers. In a further embodiment, such an output amplifier may include one or a plurality of electron multiplying charge-coupled device (EMCCD) stages (e.g., in which an amplifier section is implemented between a shift register and an output amplifier). The EMCCD stages are distinguished by almost lossless signal transfer and multiplication of the signal strength, such that the sequence signals are scarcely attenuated or corrupted.

Transferring each sequence signal into the shift register may be carried out, for example, at a frequency of between 0.5 kilohertz and 10 kilohertz (e.g., at 1 kilohertz). This transfer frequency range takes account of the characteristic speed of, for example, a base of a nucleic strand when passing through a nanopore, for example, in one millisecond.

In one embodiment, the outgoing signal of the shift register and an outgoing signal of a further shift register of the same type are transferred in parallel to a collective shift register, which transfers the signals sequentially to the evaluation device. The shift registers are therefore arranged in a comb structure, where the shift registers that receive a respective sequence signal from the measurement pick-ups are connected to the collective shift register like tines. In this case, the collective shift register collects the outgoing signals from the shift registers in multivibrators.

A sequencing arrangement for detecting and/or sequencing a plurality of biopolymers includes at least one measurement variable pick-up for picking up a sequence signal of one of the biopolymers. The sequencing arrangement also includes a shift register electrically connected to each measurement variable pick-up. The respective advantages of the embodiments are evident in each case from the above description concerning the method.

In this case, the measurement variable pick-ups and the shift register may be embodied as an integrated electrical circuit (e.g., arranged on a common microchip or silicon wafer).

The sequencing arrangement according to a further embodiment also includes a plurality of nanopore arrangements having a respective nanopore and a respective measurement variable pick-up for sequencing one of the biopolymers. The respective measurement variable pick-up may be configured to pick up a tunneling current when the biopolymer is present in the nanopore.

One embodiment of the sequencing arrangement may include a respective preamplifier between each measurement variable pick-up and the shift register.

In a further embodiment, the sequencing arrangement may include at least one output amplifier for amplifying a sequence signal. The at least one output amplifier is connected downstream of the shift register. This may also include one or a plurality of EMCCD stages, for example.

In one embodiment, the sequencing arrangement includes at least one further shift register of the stated type. The shift registers are coupled to the evaluation device via a collective shift register.

BRIEF DESCRIPTION OF THE DRAWINGS

Functionally same elements bear the same reference signs in the figures. In the figures.

DETAILED DESCRIPTION

Figure 1:
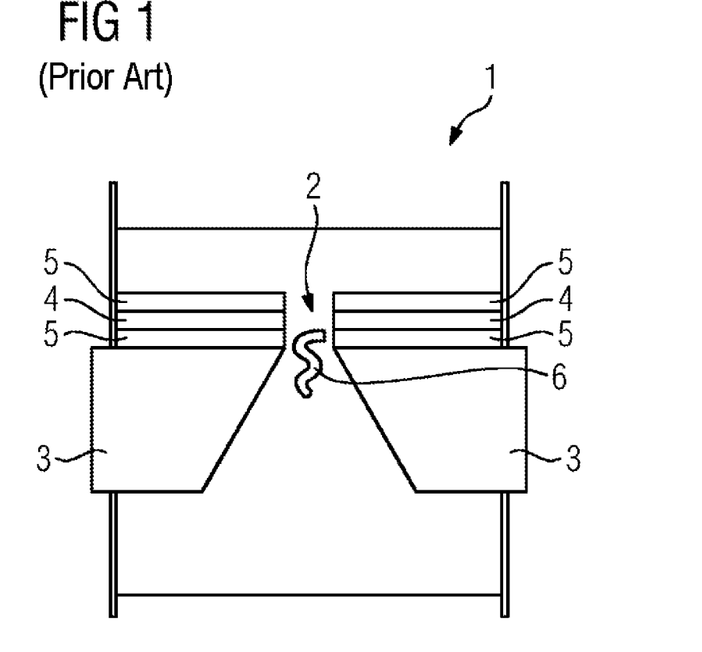
FIG. 1 shows a schematic illustration of a sequencing apparatus known from the prior art in longitudinal section.

A typical construction of a nanopore sequencer 1 from the prior art is shown in longitudinal section in FIG. 1. The sequencing device 1 includes a nanopore 2, which is produced on a silicon carrier wafer 3, for example.

Figure 2:
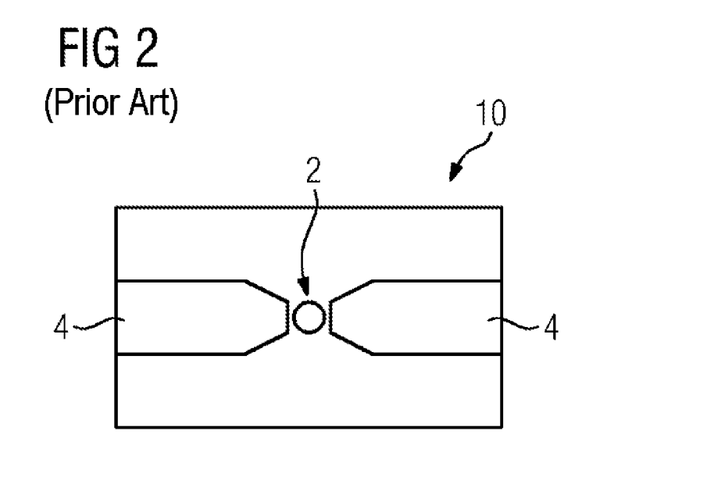
FIG. 2 shows a schematic illustration of a sequencing apparatus known from the prior art in cross section.

FIG. 2 shows a typical nanopore arrangement 10 from above. A nanopore 2 between the electrodes 4 is indicated schematically in cross section in FIG. 2. The nanopore 2 is, for example, part of a membrane (not shown in FIG. 1) between the two electrodes 4. Two tunnel electrodes 4 are fitted directly at the nanopore 2. The tunnel electrodes are arranged between insulating layers 5 in the example in FIG. 1. If a biopolymer 6 (e.g., a DNA molecule), using an applied voltage, is then drawn from the upper reservoir in FIG. 1 into the lower reservoir through the nanopore 2, a tunneling current flowing between the two tunnel electrodes 4 is modulated.

Figure 3:
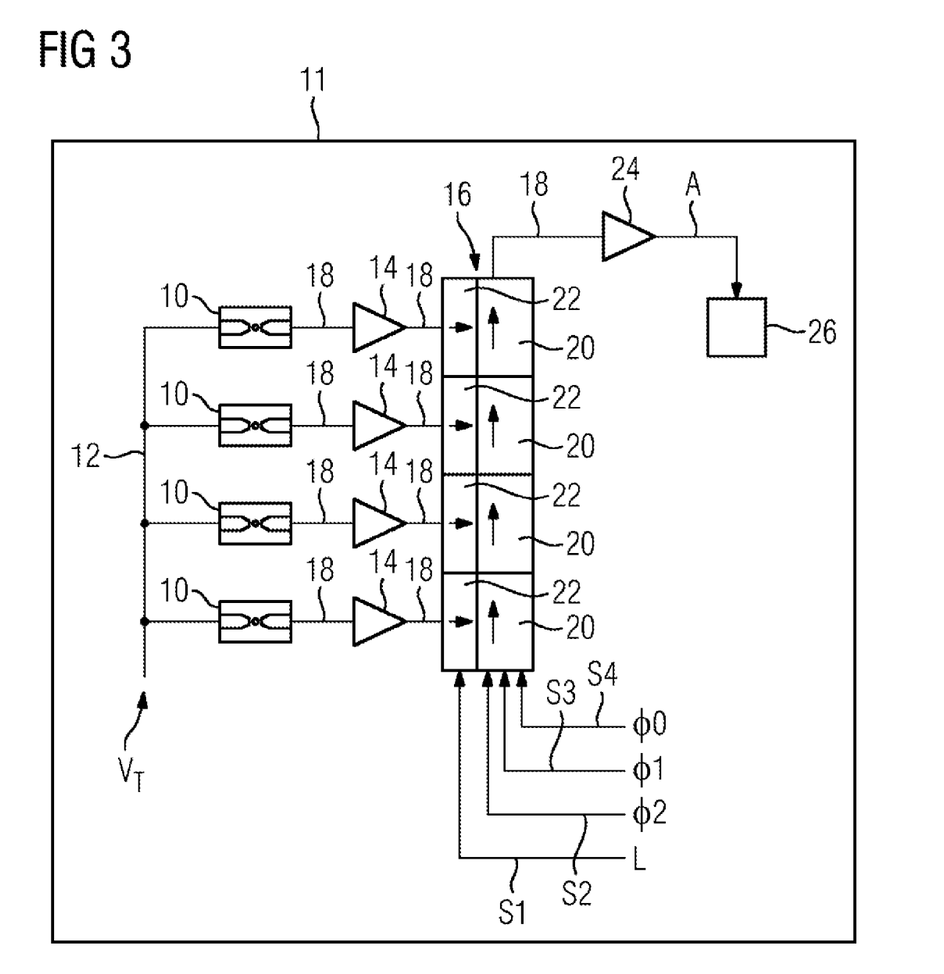
FIG. 3 shows a schematic illustration of one embodiment of a device.

FIG. 3 shows one exemplary embodiment of a sequencing arrangement 11 according to one or more embodiments, on the basis of which one exemplary embodiment of the method will be explained. There are, for example, four nanopore arrangements 10 therein, which may include, for example, a membrane with one nanopore and two electrodes flanking the nanopore, as described in FIG. 1 and FIG. 2.

A tunnel voltage ("$V_T$") is applied to a first tunnel electrode via an electrical connection 12. When a biopolymer 6 such as, for example, a nucleic acid passes through, a tunneling current flowing between the two tunnel electrodes 4 arises in each nanopore and is modulated as a sequence signal. The tunneling current is picked up by a measurement variable pick-up and transferred into a respective multivibrator 20 of a shift register 16 via an electrical connection 18.

The shift register 16 may be embodied as an analog "charge coupled device" (CCD). A shift register 16 has been known to a person skilled in the art previously as an analog shift register or as an image sensor. The shift register 16 is distinguished by almost lossless transfer of charge packets along the shift register 16. In this case, the charge transfer from individual multivibrators functions according to the bucket brigade principle. In the shift register 16, an integrated storage device 22 may be connected upstream of each multivibrator 20. The integrated storage device 22 buffer-stores and optionally amplifies a sequence signal. The respective storage device 22 may include a capacitor. In FIG. 3, the arrows within each storage device 22 indicate that the storage device 22 transfers the amplified signal into the multivibrator 20 respectively connected downstream of the storage device 22. The optionally amplified tunneling current as sequence signal may therefore be integrated in an input stage (e.g., in the storage device 22) of the shift register 16 and be accepted at periodic intervals in parallel into the shift register 16 by the activation of a "load" signal ("L") (method act S1). In this case, transferring a sequence signal into the shift register 16 may be carried out at a frequency of between 0.5 kilohertz and 10 kilohertz (e.g., at 1 kilohertz).

The content of each storage device 22 may then be shifted serially from the shift register 16 in a known manner with the aid of non-overlapping control signals "φ0", "φ1" and "φ2" for the shift register 16. An output amplifier 24 may also amplify the resultant serial AOUT signal ("A") and make the resultant serial AOUT signal available for further processing (e.g., transfer the resultant serial AOUT signal to an evaluation device 26 such as a microprocessor of a computer). However, the output signal A may also be transferred directly from the shift register 16 to the evaluation device 26. In other words, the sequence signals are sampled, and the samples, collected by the shift register 16, are transferred to an individual evaluation device 26.

In the example in FIG. 3, four nanopore arrangements are shown, but generally an arbitrary plurality of nanopore arrangements 10 connected in parallel are provided. As an alternative to a plurality of nanopore arrangements 10, a plurality of other arrangements 10 may be provided for generating a sequence signal in the method according to one or more of the present embodiments and in the device according to one or more of the present embodiments (e.g., arrangements 10 for generating a sequence signal including in each case an ion semiconductor DNA sequencing system). The plurality of nanopore arrangements 10 may be arranged, for example, in a sequencing apparatus 1 and includes a measurement variable pick-up for picking up a tunneling current of the nanopore. The sequencing apparatus 1 may likewise include, as shown in FIG. 3, the preamplifier or preamplifiers 14 and/or the shift register 16. In one embodiment, the shift register 16 and the plurality of nanopore arrangements 10 may be integrated within the same circuit (e.g., integrated on one microchip and/or in one sequencing apparatus). The advantage of such an integrated circuit resides in the almost lossless transfer of each sequence signal. Alternatively, however, the stated components may also be arranged in different apparatuses, and these apparatuses may be coupled to one another by electrical connections.

Figure 4:
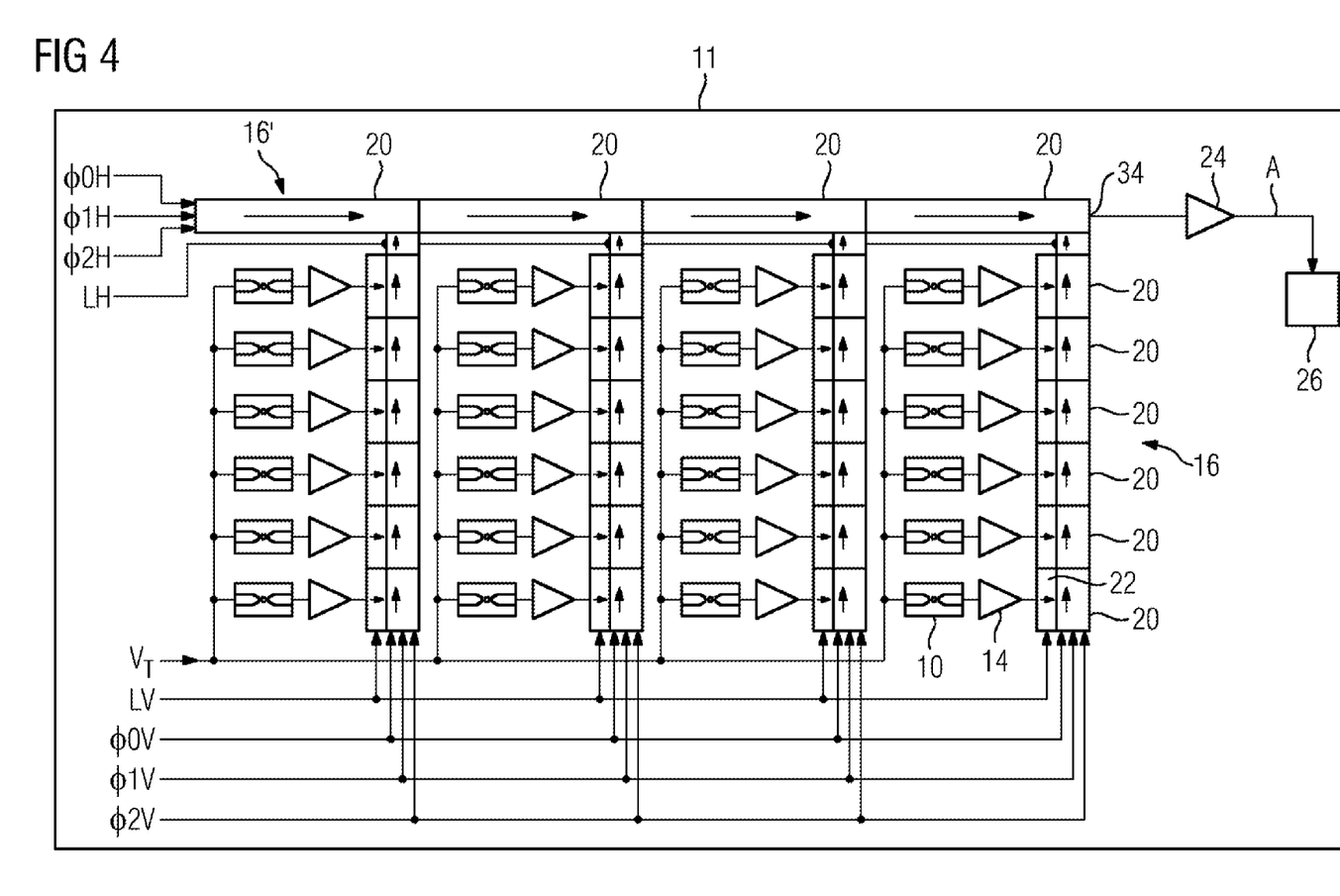
FIG. 4 shows a schematic illustration of a further embodiment of a device.

In one embodiment of the method or of the sequencing arrangement 11, a sequencing arrangement 11 according to one or more of the present embodiments may also be extended to form, for example, a sensor array or may be integrated within the same apparatus. This is shown in FIG. 4. The sequencing arrangement 11 shown in FIG. 4 is derived from the columnar arrangement from FIG. 3. For the sake of clarity, only one of the shift registers 16 connected in parallel and only a few of the nanopore arrangements 10, preamplifiers 14, input stages 22, and multivibrators 20 are identified by reference signs. The construction of a respective shift register 16 and of the respective arrangement connected upstream is evident from FIG. 3 and the associated description.

The individual columns of the arrangements (in each case including a plurality of nanopore arrangements 10 and a shift register 16) are coupled by a further shift register 16', which accepts the AOUT information of the individual columns once again in parallel into multivibrators 20' of the further shift register 16' and makes the AOUT information available serially at the output 34. A coupled arrangement, which describes the coupling together of two shift registers, is known to the person skilled in the art from EP 0 303 846 B1.

A measurement cycle may proceed as follows. First, the sequence signals are accepted into the column shift registers 16 by the activation of a "LoadV" signal ("LV"). The electrical charge of the output cell is then accepted into the row shift register 16' by the activation of the control signal "LoadH" ("LH"). As the next act, the row shift register 16' is shifted out, for example, by the control signals φ0 H, φ1 H and φ2 H for the shift register 16'. The data in the column shift registers 16 are then shifted by one position (e.g., by the control signals φ0V, φ1V and φ2V), and the read-out process at the row shift register 16' may be repeated until all the sequence signals are read out.

Figure 5:
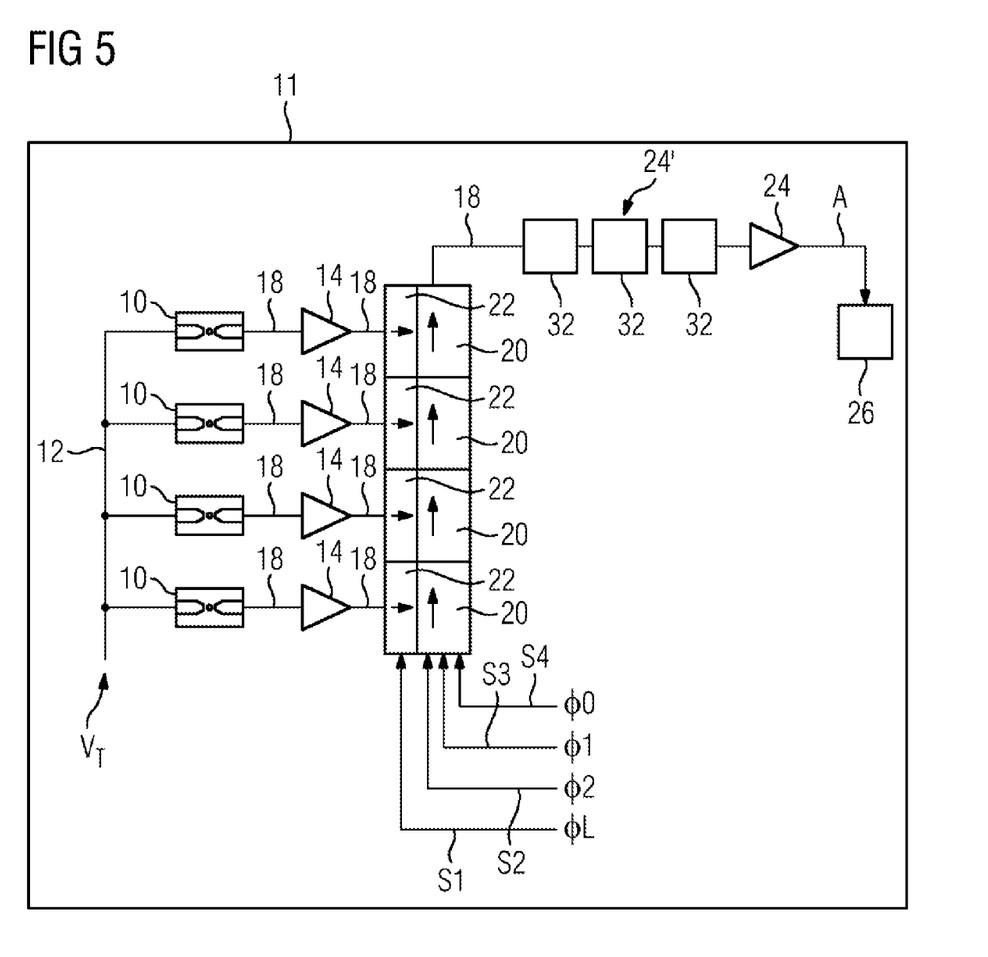
FIG. 5 shows a schematic illustration of one embodiment of a device.

In a further exemplary embodiment, which is shown in FIG. 5, the sequencing arrangement 11 according to one or more of the present embodiments may be combined with a further output amplifier 24' (e.g., an "electron multiplying CCD stage" (EMCCD)). EMCCD stages are known from camera technology. EMCCD stages are used principally in particularly sensitive camera systems. In each stage 32 of the further output amplifier 24', the number of electrons is increased from stage to stage by impact ionization. Moreover, the sequencing arrangement 11 shown in FIG. 5 may include a sequencing arrangement 11 in accordance with FIG. 3 and the associated description.

Figure 6:
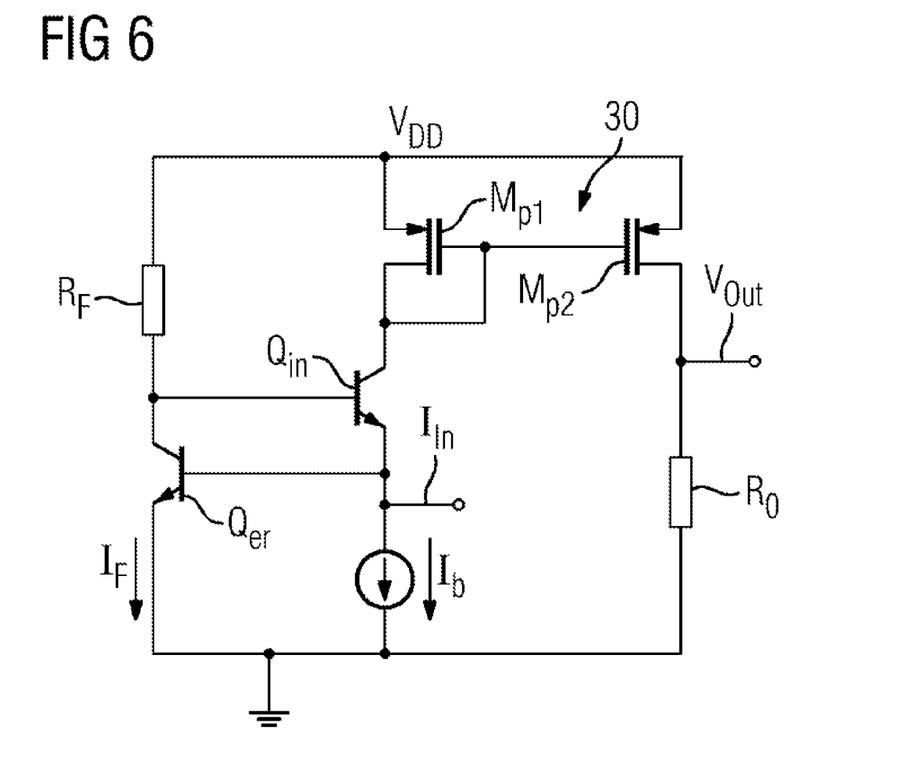
FIG. 6 shows a circuit diagram concerning a preamplifier in accordance with one exemplary embodiment.

By way of example, a transimpedance arrangement, as known from Rosenstein et al., for example, is suitable, in principle, as preamplifier 14. However, the relatively high stray capacitance of the tunnel contacts may lead to stability problems for the preamplifiers and to an increase in noise. A circuit diagram for a preamplifier 14 in the case of high input capacitances is, for example, a preamplifier 14 depicted schematically in FIG. 6. This may involve, for example, a circuit having a "common-base" input stage including a low input resistance and a current mirror 30 with respect to the output. The functioning per se is evident from the circuit diagram. By way of example, the two transistors $Q_{in}$ and $Q_{er}$ form the input stage. The signal may be brought to the output via the two current mirror transistors $M_{p1}$ and $M_{p2}$. In the example, $I_b$ is the bias current, $R_f$ is a feedback resistance, and $R_o$ is an output resistance. $I_{in}$ represents an input current, and Vow represents the output voltage.

The exemplary embodiments presented above illustrate a principle of the present embodiments (e.g., combining an arrangement for sequencing, such as a nanopore arrangement, with principles from image sensor technology).

As a result, an integrated arrangement in which, for example, an array of nanopores 4 is combined with, for example, amplifiers 14, 24 and a read-out unit 26, such that the possible throughput of one or a plurality of arrangements for sequencing is significantly increased.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for sequencing at least two biopolymers, the method comprising:
    for each biopolymer of the at least two biopolymers, picking up a sequence signal by a respective measurement variable pick-up depending on a sequence of the biopolymer, wherein picking up the sequence signal of a first biopolymer of the at least two biopolymers is carried out at the same time as picking up the sequence signal of a second biopolymer of the at least two biopolymers;
    amplifying at least the sequence signal of the first biopolymer and the sequence signal of the second biopolymer by respective preamplifiers;
    transferring at least the amplified sequence signal of the first biopolymer and the amplified sequence signal of the second biopolymer into a shift register, the shift register comprising a plurality of integrated storage devices and a plurality of multivibrators, the plurality of multivibrators being connected in series, and buffer-storing at least the amplified sequence signal of the first biopolymer and the amplified sequence signal of the second biopolymer by respective integrated storage devices of the shift register, wherein at least the respective integrated storage devices of the plurality of integrated storage devices are operable to further amplify the sequence signal of the first biopolymer and the sequence signal of the second biopolymer and transfer the sequence signal of the first biopolymer and the sequence signal of the second biopolymer to respective multivibrators of the plurality of multivibrators;
    sequentially transferring the buffer-stored sequence signals from the shift register into an evaluation device; and
    evaluating the buffer-stored sequence signals by the evaluation device.

2. The method of claim 1, wherein transferring each sequence signal into the shift register comprises transferring each sequence signal into the shift register within an integrated electrical circuit formed by the shift register and the measurement variable pick-up.

3. The method as claimed in claim 1, wherein picking up the sequence signal is carried out with the aid of a nanopore arrangement, the nanopore arrangement comprising a respective nanopore for sequencing one biopolymer of the at least two biopolymers, the respective sequence signal describes a tunneling current in the nanopore, or a combination thereof.

4. The method as claimed in claim 1, wherein sequentially transferring the buffer-stored sequence signals comprises singly or multiply amplifying each sequence signal by one or a plurality of output amplifiers.

5. The method as claimed in claim 1, wherein transferring each sequence signal into the shift register comprises transferring each sequence signal into the shift register at a frequency of between 0.5 kilohertz to 10 kilohertz.

6. The method of claim 5, wherein transferring each sequence signal into the shift register comprises transferring each sequence signal into the shift register at 1 kilohertz.

7. The method as claimed in claim 1, wherein amplifying the sequence signals is carried out by at least one electron multiplying charge-coupled device (EMCCD) stage as output amplifier.

8. The method of claim 1, further comprising:
    transferring an outgoing signal of the shift register and an outgoing signal of a further shift register of a same type in parallel to a collective shift register; and
    sequentially transferring, by the collective shift register, the outgoing signal of the shift register and the outgoing signal of the further shift register to the evaluation device.

9. A sequencing arrangement for detecting, sequencing, or detecting and sequencing a plurality of biopolymers, the sequencing arrangement comprising:
    at least one measurement variable pick-up operable to pick up a respective sequence signal of each biopolymer of the plurality of biopolymers at the same time;
    at least one preamplifier operable to amplify the respective sequence signal of each biopolymer of the plurality of biopolymers; and
    a shift register electrically connected to each measurement variable pick-up of the at least one measurement variable pick-up and operable to receive the respective sequence signals of each biopolymer of the plurality of biopolymers from a respective measurement variable pick-up after being amplified by a respective preamplifier of the at least one preamplifier, wherein the shift register comprises a plurality of multivibrators and a plurality of integrated storage devices, the plurality of integrated storage devices operable to buffer-store and further amplify the respective sequence signals of each biopolymer of the plurality of biopolymers and transfer the respective sequence signals of each biopolymer to respective multivibrators of the plurality of multivibrators.

10. The sequencing arrangement of claim 9, wherein the at least one measurement variable pick-up and the shift register are configured as an integrated electrical circuit.

11. The sequencing arrangement of claim 9, further comprising a plurality of nanopore arrangements having a respective nanopore and a respective measurement variable pick-up for sequencing the biopolymers, wherein the respective measurement variable pick-up is configured to pick up a tunneling current when the biopolymer is present in the respective nanopore.

12. The sequencing arrangement of claim 9, wherein a respective preamplifier of the at least one preamplifier is connected between each measurement variable pick-up and the shift register.

13. The sequencing arrangement of claim 9, further comprising at least one output amplifier operable to amplify a sequence signal that is connected downstream of the shift register.

14. The sequencing arrangement of claim 9, further comprising at least one further shift register of a same type as the shift register, wherein the shift register and the at least one further shift register are coupled to the evaluation device via a collective shift register.

15. The method of claim 1,
    wherein at least the sequence signal of the first biopolymer and the sequence signal of the second biopolymer are transferable to the respective multivibrators of the plurality of multivibrators corresponding to the respective measurement variable pick-ups.

16. The sequencing arrangement of claim 9,
    wherein the respective multivibrators of the plurality of multivibrators are operable to receive the respective sequence signals of each biopolymer of the plurality of biopolymers from the respective measurement variable pick-ups.

\* \* \* \* \*